USOO5391765A

United States Patent [19]
Pearce et al.

[11] Patent Number: 5,391,765
[45] Date of Patent: Feb. 21, 1995

[54] CHOLESTEROL LOWERING/ANTIOXIDANT NITROXIDES

[75] Inventors: Bradley C. Pearce, East Hampton; John J. Wright, Guilford, both of Conn.

[73] Assignee: Bristol-Myers Squibb Company, New York, N.Y.

[21] Appl. No.: 48,717

[22] Filed: Apr. 16, 1993

[51] Int. Cl.$^6$ .................. C07D 207/46; A61K 31/40
[52] U.S. Cl. .................................... 548/542
[58] Field of Search .................. 548/542; 514/424

[56] References Cited

U.S. PATENT DOCUMENTS 5,217,992 6/1993 Wright ........................... 514/458

OTHER PUBLICATIONS

Qureshi, A. A., "Dietary Tocotrienols...", *Am J Clin Nutr,* 53, pp. 10425-10465, 1991.

A. A. Qureshi, "Lowering of Serum Cholesterol...", *Am J Clin Nutr,* 53, pp. 10215-10265, 1991.

B. C. Pearce, "Hypercholesterolemic Activity...", *J. Med. Chem.,* 35, pp. 3595-3606, 1992.

Nutrition: An Integrated Approach, Ruth Pike, 1984, pp. 531-534.

*Primary Examiner*—C. Warren Ivy
*Assistant Examiner*—D. Margaret M. Mach
*Attorney, Agent, or Firm*—Prabodh I. Almaula

[57] ABSTRACT

The present invention relates to novel nitroxides which are useful for cholesterol lowering and as antioxidant agents. Also provided is a process for preparing the nitroxides of the present invention, pharmaceutical compositions, and a method of treating or inhibiting hypercholesterolemia, hyperlipidemia, atherosclerosis, and LDL oxidation which comprises administering to birds and mammals, in need of such treatment an effective amount of a compound of the present invention.

5 Claims, No Drawings

CHOLESTEROL LOWERING/ANTIOXIDANT NITROXIDES

BACKGROUND OF THE INVENTION

1. Field of the Invention

The present invention provides novel nitroxides which are effective as LDL lowering agents and which also have antioxidant capacity.

2. Description of the Art

It is generally recognized that high blood cholesterol levels are significant risk factors in cardiovascular disease.

It has been established that 3-hydroxy-3-methylglutaryl coenzyme A reductase (HMGR) is the first rate limiting enzyme in the biosynthetic pathway for cholesterol, that inhibition of HMGR activity results in a decrease in serum total cholesterol and low density lipoprotein (LDL) cholesterol levels, and that a decrease in serum LDL-cholesterol levels is reflected in a reduction of plasma level of apolipoprotein B. (Brown, et al, J. Lipid Res, 21: 505–517 (1980)).

Tocotrienols have been shown to suppress HMGR resulting in the inhibition of cholesterol biosynthesis and a subsequent drop in LDL cholesterol, apolipoprotein B, thromboxane $B_2$, platelet factor 4 and glucose levels. (Wright, et al, *A Symposium On Drugs. Affecting Lipid Metabolism*, Houston, Tex. (November 1989)).

The tocotrienols are structurally related to the tocopherols (vitamin E) and differ only by possessing unsaturation in the isoprenoid side chain. Like the tocopherols, the tocotrienols have antioxidative activity. (Yamaoka, et al, *Yukagaku*, 3.4: 120–122 (1985); Serbinova, et al, *Free Radical Biology and Medicine*, 10: 263–275 (1991)).

Active oxygen species are known to play pivotal roles in the genesis of atherosclerotic plaques, thrombotic episodes, ischemic damage, cancer, aging, dementia, and inflammatory conditions. (Sies, H., *Oxidative Stress*; Academic Press, New York, (1985); Santrucek, M., Krepelka, J., *Drugs of the Future*, 13: 973–996 (1988); Steinberg, *Circulation*, 84: 1400–24 (1991)). Of particular interests are the potential protective effects of antioxidants on lipoproteins, since oxidized LDL is thought to be atherogenic. (Buckley et. al., *Drugs*, 37: 761–800 (1989); Gwynne et. al., *Am. J. Cardiology*, 62: 1B-77B (1988)).

PROBUCOL (4,4'-[(1-methylethylidene)bis(thio)]-bis[2,6-bis(1,1-dimethylethyl)] (Lorelco, Marion Merrell Dow) (Formula I) is a hypolipidemic drug, which is also an excellent antioxidant. PROBUCOL inhibits the oxidative modification of LDL both in vitro and in vivo. (Steinberg, *Am. J. Cardiol.*, 57: 16H-21H (1986)). PROBUCOL, however, suffers from bioavailability problems, exhibits only modest reductions in LDL cholesterol, and has undesirable effects on HDL cholesterol.

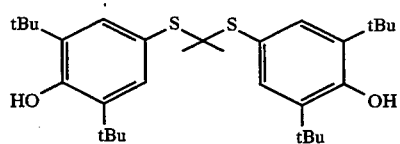

Formula I

Esterbauer et al. (Dieber-Rotheneder, et al., *J. Lipid Res.*, 2: 1325–32 (1991)) have examined the oxidative resistance of LDL as a function of oral vitamin E supplementation. While the oxidative resistance of LDL was significantly enhanced during vitamin E supplementation, antioxidant effectiveness varied considerably from subject to subject.

Nitroxides have been used for years as spin labels for probing the structure of biological membranes. Recently, the capacity of nitroxides to function as superoxide dismutase (SOD) mimetics has gained attention in the literature. (Samuni, et al., *J. Biol. Chem.*, 263: 17921–24 (1988) and Mitchell, et al., *Biochemistry*, 29: 2802–2807 (1990)). An international patent application has been filed by Pharmacia AB for the use of low molecular weight nitroxides as antiischemic agents (myocardial)(PCT/SE87/00629). The metabolic pathways of nitroxides have been recently reviewed (Schwartz, *Free Rad. Res. Comms.*, 9: 399–405 (1990)). Nitroxides are readily reduce in vivo to give hydroxylamines, which are in turn capable of oxidation back to nitroxides. This redox transfer is mediated by enzymatic pathways in the mitochondria. The nitroxide/hydroxylamine shuttle has interesting implications for the design of lipid peroxidation inhibitors (Nilsson, et al., *J. Biol. Chem.*, 264: 11131–35 (1989) and Nilsson, et al., *Chem.-Biol. Interactions*, 74: 325–42 (1990)).

While the causative factors in the development of atherosclerosis are many, two important ones are elevated serum cholesterol levels and excessive LDL oxidation.

The present invention provides novel compounds which maximize cholesterol biosynthesis inhibition and antioxidant efficiency within the same molecule. The compounds of the present invention generally have greater bioavailability and antioxidant capacity than PROBUCOL.

SUMMARY OF THE INVENTION

The present invention provides novel nitroxides which combine lipid lowering with antioxidant effectiveness.

An aspect of the present invention provides nitroxides which are useful for cholesterol/lipid lowering in cases of hypercholesteremia, hyperlipidemia and atherosclerosis, and which are useful to inhibit LDL oxidation.

Another aspect of the present invention provides a pharmaceutical composition which comprises at least one compound of the present invention and a non-toxic pharmaceutically acceptable carrier.

Another aspect of the present invention provides a method of treating hypercholesteremia, hyperlipidemia and thromboembolic disorders in birds and mammals, including humans, which consists of administering at least one compound of the present invention to a host in need of such treatment.

Another aspect of the present invention provides a method of inhibiting cholesterol biosynthesis, lowering LDL cholesterol, and inhibiting LDL oxidation in birds and mammals, including humans, which consists of administering at least one compound of the present invention to a host in need of such treatment.

These and other advantages and objects of the invention will be apparent to those skilled in the art.

DETAILED DESCRIPTION OF THE INVENTION

The present invention provides compounds of the general Formulae II and III

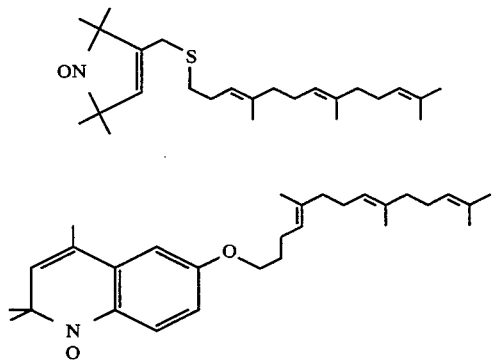

Also included within the scope of the present invention are the pharmaceutically acceptable acid addition salts, metal salts, solvates, and hydrates of the compound of Formulae II and III which may exist in various tautomeric forms.

Synthesis of the nitroxide of Formula II (3) is shown in Scheme I, and begins with the known thiol 2 (Hideg, et al., *Synthesis*, 911–914 (1980) and Hankovszky, et al., i Synthesis, 914–916 (1980)). Thiol 2 can be prepared in four steps from commercially available 3-carboxy-2,2,5,5-tetramethyl-2,5-dihydropyrrole-1-oxyl 1 (Eastman Kodak). The side chain was linked by alkylation to homofarnesyl iodide.

Scheme I

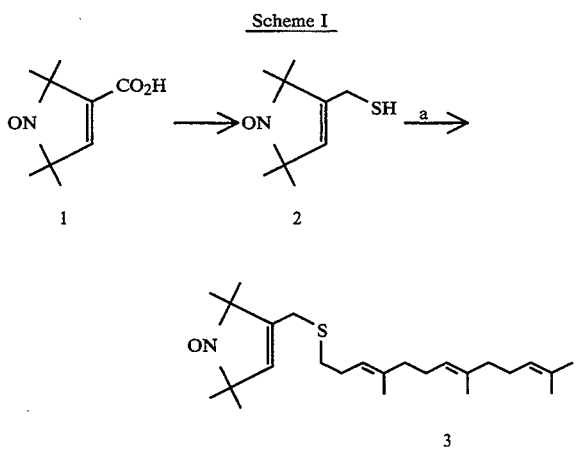

a) Homofarnesyl iodide, potassium carbonate, acetonitrile

The compound of Formula III (5) was prepared from 1,2-dihydro-2,2,4-trimethyl-6-[(5,9,13-trimethyl-4(E), 8(E),12-tetradecatrienyl)oxy]quinoline (4) by treatment with hydrogen peroxide in the presence of sodium tungstate. [Scheme II]

Scheme II

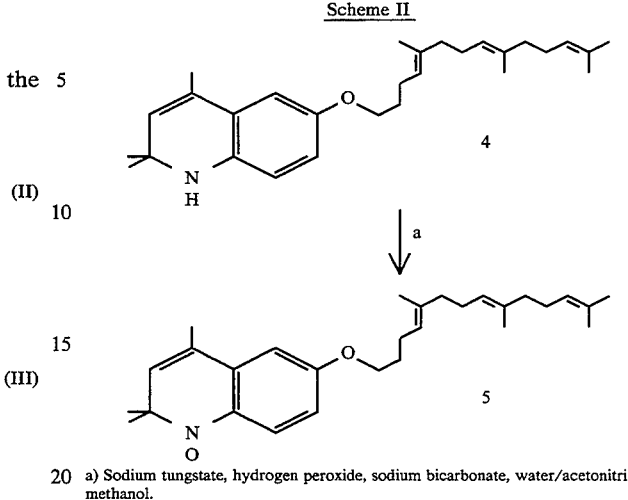

a) Sodium tungstate, hydrogen peroxide, sodium bicarbonate, water/acetonitrile/methanol.

HepG2 Cell Culture Model

The human hepatoma HepG2 cell culture model was employed to compare the intrinsic activities of the synthetic analogues relative to the tocotrienols. HepG2 cells were incubated with the indicated compounds for 4 hours at 10 µM. Cholesterol synthesis was assayed by $^{14}$C-acetate incorporation over the final hour of incubation, and HMG-CoA reductase suppression (specific activity) was assayed in the microsomal fraction isolated from parallel cultures at the end of the 4 hour incubation. Time course studies indicated that 4 hours preincubations provided maximal suppression of sterol synthesis. (Table I)

TABLE I

| Compound 10 µM | Percent of Control | |
|---|---|---|
| | Chol. Biosynthesis | HMGR Suppression |
| γ-Tocotrienol | 75 | 65 |
| 3 | 5 | 45 |
| 5 | 72 | N.T. |

N.T. = Not Tested.

In Vivo Evaluation of Synthetic Analogues in Normocholesterolemic Chickens

Hypocholesterolemic activity was evaluated for the synthetic analogues using γ-tocotrienol as a control in normocholesterolemic chickens. Newborn male chicks (6–10 for each group) were raised on a standard corn-soybean-based control diet for two weeks and then were switched to either control or experimental diets for four weeks. Drug treatment consisted of the addition of test compound to the corn-soybean-based. At the end of the feeding period, all the birds were fasted (about 36 hours) and refed (about 48 hours) to induce cholesterolgenic enzymes prior to sacrifice. The specific activity of HMG-CoA reductase, total serum cholesterol levels, HDL/LDL cholesterol pools, and triglyceride levels (data not shown) were examined (Table II).

TABLE II

Effects of Compound 3 on Lipid Parameters in Male Chickens Orally dosed for 4-weeks at 4 mg/kg/day

| Compound | Values Given as % of Control | | | |
|---|---|---|---|---|
| | Tot.-C | LDL-C | HDL-C | HMGR |
| γ-Tocotrienol | 76.3 | 54.8 | 87.0 | N.T. |

TABLE II-continued

Effects of Compound 3 on Lipid Parameters in Male Chickens Orally dosed for 4-weeks at 4 mg/kg/day

| Compound | Values Given as % of Control | | | |
|---|---|---|---|---|
| | Tot.-C | LDL-C | HDL-C | HMGR |
| 3 | 72.0 | 52.8 | 85.8 | 56.0 |

N.T. = Not Tested

Antioxidant Evaluation

There are a number of ways in which one can evaluate a biological antioxidant. (Halliwell, *Free Rad. Res. Comms.*, 9: 1–32 (1990)). The ability of test compounds to inhibit the oxidative modification of LDL is what is most relevant here. (Bedwell, et al., *Biochem. J.*, 262: 707–712 (1989)). The oxidative modification of LDL has been examined in vitro, using both copper and cellular (enzymatic) mediated processes. Esterbauer et al. (Esterbauer, et al., *Free Rad. Res. Comms.*, 6: 67–75 (1989)) have developed a conjugated diene assay for the measurement of LDL Oxidation. The oxidation of polyunsaturated lipids causes the conjugation of double bonds that can be quantitatively measured spectrophotometrically. The conjugated diene assay appears to be superior to older methods such as the measurement of thiobarbituric acid reactive substances (TBARS). (Yagi, *Chem. Phys. Lipids*, 45: 337–351 (1987)). A third method that has been employed, measures lipid peroxides directly, and uses the very sensitive peroxidase-coupled tetramethyl benzidine (TMB) assay. (Tetramethyl Benzidine TMB).

One method for the measurement of general antioxidant capacity is stopped-flow kinetic analysis. (Mukai, et al., *Bull. Chem. Soc. Jpn.*, 59: 3113–3116 (1986); Mukai, et al., *J. Org. Chem.*, 54: 557–560 (1989); Mukai, et al., *J. Org. Chem.*, 53: 430–432 (1988)). This is a sophisticated setup wherein, one measures radical transfer from a stable radical (for example, 2,6-di-tert-butyl-4-(4-methoxyphenyl)phenoxy) to a test compound spectrophotometrically as a function of time. Mukai et al. have demonstrated that a linear relationship exists between second-order rate constants derived from stopped-flow measurements and their half-peak oxidation potentials as measured voltammetrically. Voltammetry has been used by Moldeus et al. (Cotgreave, et al., *Biochem. Pharm.*, 2: 1481–85 (1991)) to study the antioxidant capacity of structurally related dibenzo[1,4] dichalcogenines as inhibitors of lipid peroxidation. In their case, a strong correlation between voltammetric potential and the ability to inhibit lipid peroxidation was observed.

Redox Potential and In Vitro LDL Oxidation

The general antioxidant capacity of several reference agents and the compounds of the present invention as measured by cyclic voltammetry is shown in Table III. A linear dependence of oxidation potentials to hydrogen atom donation capacity exists for compounds of similar structure. The lower the oxidation potential (voltage) the easier the compound is to oxidize. For the in vitro LDL oxidation assay, test compounds were incubated (10 μM) with fresh plasma derived from rabbits maintained on a diet which enriches LDL in linoleate content; LDL was then isolated from the treated plasma, dialyzed, and incubated under oxidizing conditions (added Cu++). Oxidation was measured spectrophotometrically by conjugated diene formation and the lag time extension versus control (ratio of treated/control) was determined from the first derivative of the $A_{234}$ kinetic curves.

TABLE III

Redox Potential and In Vitro LDL Oxidation

| Compound | Oxd. Potential Volts | n | LDL Oxd. Inhib. mean lag ratio |
|---|---|---|---|
| Butylatedhydroxytoluene | | 1 | 1.38 |
| PROBUCOL | 1.12 | 28 | 1.38 |
| ETHOXYQUIN | | 1 | 1.21 |
| Ascorbate | | 1 | 1.00 |
| α-Tocopherol | 0.81 | 5 | 1.01 |
| γ-Tocopherol | | 2 | 1.17 |
| γ-Tocotrienol | 0.94 | 3 | 1.27 |
| 3 | 0.65 | 2 | 0.97 |

The results to the above tests demonstrate that the compounds of Formulae II and III inhibit HMGR activity which results in a decrease in serum total cholesterol, a decrease in LDL cholesterol levels, and inhibition of LDL oxidation.

Thus, the compound of Formulae II and III may be readily administered, to treat hypercholesterolemia, hyperlipidemia, and atherosclerosis, and to inhibit LDL oxidation in avian and mammalian systems in need of such treatment. For this purpose, the drug may be administered by conventional routes including, but not limited to, the alimentary canal in the form of oral doses, by injection in sterile parenteral preparations on nasally.

In yet another aspect, the present invention provides a pharmaceutical composition which comprises a compound of Formulae II or III and a non-toxic pharmaceutically acceptable carrier. These carriers can be solid or liquid such as cornstarch, lactose, sucrose, olive oil or sesame oil. If a solid carrier is used, the dosage forms may be tablets, capsules, powders, troches or lozenges. If the liquid form is used, soft gelatin capsules, syrup or liquid suspensions, emulsions, or solutions in convenient dosage forms may be used. The composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiologically saline or some other sterile injectable medium immediately before use.

The dosage ranges will commonly range from about 50 mg to about 200 mg. Optimal dosages and regimes for a given host can be readily ascertained by those skilled in the art. It will, of course, be appreciated that the actual dose used will vary according to the particular composition formulated, the particular compound used, the disease being treated. Many factors that modify the action of the drug will be taken into account including age, weight, sex, diet, time of administration, route of administration, rate of excretion, condition of the patient, drug combinations, reaction sensitivities and severity of the disease.

All publications cited in this specification are indicative of the level of skill of those skilled in the art to which this invention pertains. Each publication is individually incorporated herein by reference in the location where it is cited.

The following examples are intended for illustrative purpose only and are not to be construed as limiting the invention in sphere or scope.

Melting points were recorded on a Thomas-Hoover melting point apparatus and are uncorrected. Boiling points are uncorrected. Infrared spectra were obtained on a Perkin-Elmer Model 1800 FT-IR spectrophotometer. $^1$H-NMR spectra were recorded on a Bruker AM 300 spectrometer or a Varian Gemini 300 NMR spectrometer; nuclear magnetic resonance (NMR) spectral characteristics refer to chemical shifts ($\delta$) expressed in parts per million (ppm) with tetramethylsilane (TMS) as an internal standard. The relative area reported for the various shifts in the proton NMR spectral data corresponds to the number of hydrogen atoms of a particular functional type in the molecule. Mass spectra were measured on a Finnegan 4500 spectrometer (low resolution).

Thin-layer chromatography was performed on silica gel 60 F-254 plates purchased from E. Merck and company (visualization with iodine or phosphomolybdic acid); flash chromatography was performed on fine silica (EM Sciences, 230-240 mesh). All reactions were run under dry nitrogen unless otherwise indicated. Dry solvents were purchased from Aldrich, Milwaukee, Wis. in sure/seal bottles and transferred by syringe under nitrogen. Most commercially available starting materials did not require further purification.

EXAMPLE 1

2,5-Dihydro-2,2,5,5-Tetramethyl-3-[[(4,8,12-Trimethyl-3(E),7(E),11-Tridecatrienyl)thio]methyl]-1H-Pyrrole N-Oxide Radical, (3)

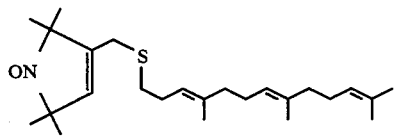

3-Mercaptomethyl-2,2,5,5-tetramethyl-2,5-dihydropyrrole-1-ox yl (Hideg, et al., Synthesis, 911–914 (1980); Hankovszky, et al., Synthesis, 914–916 (1980)) (486 mg, 2.61 mmole), homofarnesyl iodide (764 mg, 3.4 mmole), and potassium carbonate (721 mg, 5.22 mmole) were stirred in 6 mL of acetonitrile for about 3 days at about 23°. The reaction mixture was poured into water (100 mL) and the aqueous layer extracted with ether. The organic extracts were combined, dried (brine, MgSO$_4$) and concentrated in vacuo. The residue was purified by flash chromatography [gradient 8:1 to 4:1 Hexanes:Ether] to give BMY 46642 (720 mg, 1.78 mmole, 68%): IR (film) 2974, 2926, 1442, 1356, 840 cm$^{-1}$; MS m/e 405 (MH+).

Anal. HRMS, calcd. 404.2987. Found: 404.2995.

EXAMPLE 2

1,2-Dihydro-2,2,4-Trimethyl-6-[(5,9,13-Trimethyl-4(E),8(E),12-tetradecatrienyl)oxy]Quinoline, (4)

6-Ethoxy-2,2,4-trimethyl-3,4-dihydroquinoline [Ethoxyquin, Tokyo Kasai] (70 g, 0.32 mole), was added to 250 mL of 48% HBr, and the mixture was heated to reflux for about 1 hour. The solution was cooled and poured into water. The aqueous suspension was made basic (pH=14) by the addition of 50% aqueous NaOH. Concentrated HCl was added to adjust the pH to about 4, then the mixture was made slightly basic by the addition of saturated sodium bicarbonate solution. The mixture was extracted with EtOAc and the organic layers were dried (brine, MgSO$_4$) and concentrated in vacuo. The thick dark oil was triturated with toluene and the insoluble residue was filtered. The crude solid was recrystallized from toluene to give 6-hydroxy-1,2-dihydro-2,2,4-trimethylquinoline as a light brown solid (mp 182°–184°, 34 g, 0.18 mole, 56%). An analytical sample was prepared by another recrystallization from toluene to provide light brown crystals, mp 182°–184°: IR (KBr) 3302, 2972, 2934, 1586, 1495, 1344, 1244, 1154, 880, 814 cm$^{-1}$; $^1$H NMR (D-6 DMSO) $\delta$1.12 (s, 6H), 1.33 (s, 3H), 3.34 (s, 1H), 5.17 (br s, 1H), 5.26 (s, 1H), 6.28–6.42 (m, 3H); MS m/e 190 (MH+).

Anal. Calcd. for $C_{12}H_{15}N_1O_1$: C, 76.16; H, 7.99; N, 7.40. Found: C, 76.29; H, 7.95; N, 7.37.

6-Hydroxy-1,2-dihydro-2,2,4-trimethylquinoline (12 g, 0.064 mole), and sodium acetate (10.4 g, 0.13 mole) were stirred in 75 mL of acetic anhydride at 100° for about 3 hours. The mixture was poured into water and extracted into ether. The ether extracts were combined and successively washed with water, aqueous NaHCO$_3$, dried (brine, MgSO$_4$) and concentrated in vacuo. Purification of the crude material by flash chromatography [5:1 Hexanes:Et$_2$O] yielded the diacetyl derivative as a dark yellow oil: $^1$H NMR (CDCl$_3$) $\delta$1.48 (s, 6H), 1.95 (s, 3H), 2.12 (s, 3H), 2.27 (s, 3H), 5.5 (s, 1H), 6.76–6.90 (m, 3H).

The diacetyl derivative (12 g) was dissolved in 100 mL of ether. The ether solution was cooled to about −78° and 1M KOH/MeOH (20 mL) was added. The reaction mixture was stirred at −78° for about 1 hour at which time TLC indicated the reaction to be complete. The solution was poured into 1N HCl and extracted into ether. The ether extracts were dried (brine, MgSO$_4$) and concentrated in vacuo. The resulting solid was recrystallized from acetonitrile to give 1-acetyl-6-hydroxy-1,2-dihydro-2,2,4-trimethylquinoline as an off white solid (mp 214°–216°, 5.9 g, . 0.026 mole, 40%): IR (KBr) 3126, 2972, 1626, 1596, 1460, 1368, 1344, 1252, 1218, 868 cm$^{-1}$; $^1$H NMR (CDCl$_3$) $\delta$1.20 (s, 6H), 1.70 (s, 3H), 1.80 (s, 3H), 5.23 (s, 1H), 6.34–6.44 (m, 3H), 8.61 (s, 1H); MS m/e 232 (MH+).

Anal. Calcd. for $C_{14}H_{17}N_1O_2$: C, 72.70; H, 7.41; N, 6.06. Found: C, 72.89; H, 7.46; N, 6.09.

1-Acetyl-6-hydroxy-1,2-dihydro-2,2,4-trimethylquinoline (4.0 g, 17.3 mmole), farnesyl ethanol (4.3 g, 17.3 mmole), and triphenylphosphine (5.0 g, 19.0 mmole) were dissolved in 30 mL of THF. Diethylazodicarboxylate (3.3 g, 19.0 mmole) was added dropwise over 5 minutes, and the solution was stirred at about 23° for about 40 hours. The volatile components were removed in vacuo and the oily solid was triturated with ether. The solid was removed by filtration and the residue was purified by flash chromatography [gradient 6:1 to 5:1 Hexanes: Ether ] to yield 1-acetyl-1,2-dihydro-2,2,4-trimethyl-6-[(5,9,13-trimethyl-4(E) ,8(E) ,12 -tetradecatrienyl)oxy]quinoline as a yellow oil (6.1 g, 13.2 mmole, 76%): IR (film) 2924, 1672, 1606, 1492, 1364, 1324, 1204 cm$^{-1}$; $^1$H NMR (CDCl$_3$) $\delta$1.50 (s, 6H), 1.59 (s, 6H), 1.61 (s, 3H), 1.68 (s, 3H), 1.83 (m, 2H), 1.94–2.14 (m, 8H), 2.01 (s, 3H), 2.11 (s, 3H), 2.17 (m, 2H), 3.95 (t, J=6.4 Hz, 2H), 5.08–5.19 (m,3H), 5.54 (s, 1H), 6.65–6.79 (m, 3H); MS m/e 464 (MH+).

Anal. Calcd. for $C_{31}H_{45}N_1O_2$: C, 80.30; H, 9.78; N, 3.02. Found: C, 80.03; H, 9.70; N, 3.04.

1-Acetyl-1,2-dihydro-2,2,4-trimethyl-6-[(5,9,13-trimethyl-4(E),8(E),12-tetradecatrienyl)oxy]quinoline (8.2 g, 17.7 mmole) was dissolved in 75 mL of THF and the solution was cooled to about −10°. Lithium triethylborohydride (1.0M, 89 mL, 89 mmole) was added dropwise to the mixture and the cooling bath was removed. After stirring at about 23° for about 60 hours, the reaction was quenched by the careful addition of saturated NH4Cl solution. The mixture was poured into water and extracted into ether. The ether extracts were dried (brine, MgSO4) and concentrated in vacuo. Purification of the crude material by flash chromatography [20:1 Hexanes:ET$_2$O] yielded the dihydroquinoline as a yellow oil (6.2 g, 12.8 mmole, 72%): IR (film) 3364, 2964, 1650, 1580, 1498, 1446, 1380, 1260, 1156 cm$^{-1}$; $^1$H NMR (CDCl$_3$+TFA) δ1.50 (s, 6H), 1.57 (s, 6H), 1.59 (s, 3H), 1.65 (s, 3H), 1.85 (m, 2H), 1.94–2.14 (m, 8H), 2.07 (s, 3H), 2.16 (m, 2H), 3.94 (t, J=6.3 Hz, 2H), 5.0 (m,3H), 5.63 (s, 1H), 6.76 (d of d, J=2.5, 8.6 Hz, 1H), 6.88 (d, J=2.5 Hz, 1H), 7.32 (d, J=8.6 Hz, 1H); MS m/e 422 (MH+).

Anal. Calcd. for C$_{29}$H$_{43}$N$_1$O$_1$: C, 82.61; H, 10.28; N, 3.32. Found: C, 82.71; H, 10.40; N, 3.21.

EXAMPLE 3  1,2 -Dihydro-2,2,4-Trimethyl-6-[(5,9,13 -Trimethyl-4(E),8(E),12-tetradecatrienyl) oxy]Quinoline N-Oxide Radical, (5)

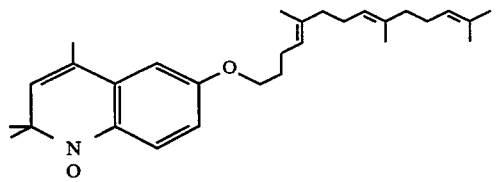

1,2-dihydro-2,2,4-trimethyl-6-[(5,9,13-trimethyl-4(E),8(E),12-tetradecatrienyl)oxy]quinoline (0.2 g, 0.48 mmole) was dissolved in MeOH (1 mL)/MeCN (0.2 mL). Sodium bicarbonate (66 mg, 0.79 mmole), sodium tungstate (10 mg, 0.003 mmole) and hydrogen peroxide (30%, 0.4 mL, 3.5 mmole) were added sequentially. The mixture was stirred for about 2 days at about 23°. The reaction mixture was poured into water (10 mL) and the aqueous layer extracted with ethyl acetate. The organic extracts were combined, dried (brine, MgSO4) and concentrated in vacuo. The residue was purified by flash chromatography [20:1 Hexanes:EtOAc] to give the title compound 5 (60 mg, 0.14 mmole, 29%): IR (film) 2974, 2926, 1580, 1442, 1365, 1280, 1250, 1150 cm$^{-1}$; MS m/e 436, 437 (M+, MH+).

Anal. Calcd. for C$_{29}$H$_{42}$N$_1$O$_2$: C, 79.77; H, 9.69; N, 3.21. Found: C, 79.56; H, 9.67; N, 2.97.

Other embodiments of the invention will be apparent to the skilled in the art from a consideration of this specification or practice of the invention disclosed herein. It is intended that the specification and examples be considered as examplary only, with the true scope and spirit of the invention being indicated by the following claims.

We claim:

1. The compound which is 2,5-dihydro-2,2,5,5-tetramethyl-3-[[(4 ,8,12-trimethyl-3(E) ,7(E) ,11-tridecatrienyl)thio]methyl]-1H-pyrrole N-oxide, or a pharmaceutical salt, solvate, or hydrate thereof.

2. A pharmaceutical composition which comprises a compound of claim 1 and a pharmaceutical acceptable carrier.

3. A method of inhibiting cholesterol biosynthesis, lowering LDL cholesterol, and inhibiting LDL oxidation which comprises administering to a host in need thereof an effective amount of a compound of claim 1.

4. The method of claim 3 wherein the host is a mammal.

5. A method of treating hypercholesterolemia, hyperlipidemia and atherosclerosis which comprises administering to a host in need thereof an effective amount of a compound of claim 1.

* * * * *